United States Patent [19]

Grangeorge et al.

[11] Patent Number: 5,118,794
[45] Date of Patent: Jun. 2, 1992

[54] PROCESS FOR STABILIZING HUMAN ALBUMIN SOLUTIONS AND THE SOLUTION OBTAINED

[75] Inventors: Michel Grangeorge, Vaugneray; Pierre Fournier, Lyons, both of France

[73] Assignee: Institut Merieux, France

[21] Appl. No.: 336,387

[22] Filed: Apr. 11, 1989

[30] Foreign Application Priority Data

Apr. 14, 1988 [FR] France ................... 88 04936

[51] Int. Cl.$^5$ ............................................. A61K 37/02
[52] U.S. Cl. .................................. 530/363; 530/362; 530/364
[58] Field of Search ............... 530/362, 363, 364; 514/21

[56] References Cited

U.S. PATENT DOCUMENTS 4,315,919  2/1982  Shanbrom .................... 530/303

FOREIGN PATENT DOCUMENTS 0050061  3/1982  European Pat. Off. .
0124044  2/1984  European Pat. Off. .
0131740  7/1985  European Pat. Off. .

OTHER PUBLICATIONS

Shrake et al., (Vox. Sang. 1984 47(1) 7-18), CA vol. 101, 1984 136888g.
Yu et al., (Vox. Sang. 1984 47(1) 28-40), CA vol. 101, 1984 136890b.

Primary Examiner—Howard E. Schain
Assistant Examiner—Choon Park Koh
Attorney, Agent, or Firm—Larson & Taylor

[57] ABSTRACT

In order to stabilize solutions of human albumin for therapeutic use for the purpose of their treatment by heat in a container, in particular in the final container, there is added, in addition to the usual stabilizing formula, a surfactant agent selected from among Tween 80, Tween 20, Pluronic F68, laurate of polyethylene glycol 600 or any other equivalent agent.

9 Claims, No Drawings

PROCESS FOR STABILIZING HUMAN ALBUMIN SOLUTIONS AND THE SOLUTION OBTAINED

The invention relates to a process for stabilizing human albumin solutions for therapeutic use for the purpose of their treatment with heat in a container, in particular in the final container.

The invention also relates to the albumin solution obtained by the process according to the invention.

In the course of the manufacture of human albumin solutions an obligatory step is the final pasteurization of the product at 60° C. for 10 hours. This heating step was introduced in the U.S.A. at the beginning of the 1950s so as to inactivate the virus of hepatitis B which may be present in the final product, despite the various purification steps, owing to the possible contamination of the biological raw material, i.e. at that time the human blood. The effectiveness of this pasteurization for eliminating or reducing the risk of transmission of the hepatitis B by the albumin solutions was originally revealed in healthy volunteers. Studies carried out with the chimpanzee subsequently showed that the virus of the non A non B hepatitis is also inactivated by a treatment at 60° C. for 10 hours. This data was the subject of a review by GERETY and ARONSON (1). Since then, various studies in vitro with the aid of model viruses have shown that the pasteurization of the protein solutions at 60° C. for 10 hours may be considered as being a rather general method for reducing the risk of viral transmission to the recipient although certain viruses, such as the parvovirus, are more resistant than others to the thermal inactivation (2-3).

Patent EP-A-0 050 061 prescribes another solution comprising, in preparations of plasmatic proteins, for example albumin, inactivating the hepatitis viruses and possibly eliminating the endotoxins by the action of surface active agents at a high concentration. This solution however does not afford the advantages of the inactivation of albumin preparations by heat.

At the present time, all of the national and international pharmacopoeias require the pasteurization of the albumin solutions at 60° C. for 10 hours, it being necessary to effect this pasteurization at the absolutely last stage of the manufacture, namely in the final container which is usually a vial of neutral glass; see for example the European Pharmacopoeia IInd edition, 1984, the Pharmacopoeia of U.S.A., XXIst edition, and the Japanese Pharmacopoeia of 1986. Notwithstanding the relative stability of albumin with regard to heat, the albumin must be protected in order to avoid any gelling during the pasteurization, with the aid of suitable stabilizers. The stabilizers employed at the present time in a almost general manner are sodium caprylate and sodium acetyl tryptophanate, alone or in combination. In particular, the U.S.A. Pharmacopoeia XXIst edition and the Japanese Pharmacopoeia of 1986 require sodium acetyl tryptophanate alone at the dose of 0.16 millimole per gram of albumin, or the mixture sodium acetyl tryptophanate/sodium caprylate each at the dose of 0.08 millimole per gram of albumin. Sodium mandelate may also be used alone or in association with sodium caprylate (see the French Pharmacopeia VIIIst edition of 1965).

The stabilizers are added in a large excess relative to the albumin, namely 10 molecules of stabilizer for 1 molecule of albumin according to the U.S.A. and Japanese Pharmacopoeias, and owing to their own affinity for the albumin, they are capable of effectively protecting it against a direct denaturing by the heat. In the absence of these stabilizers, the denaturing of the albumin is inevitable and results in a progressive aggregation of molecules of albumin which causes the appearance of an opalescence and then a complete gelling of the solution.

If this opalescence and this gelling are in fact avoided by the use of the previously-described stabilizers, it is known that, after the pasteurization, a certain number of vials of albumin have, upon visual inspection, fine flocculose particles or filaments or skins in a more or less large number. This phenomenon is more accentuated in respect of the most diluted albumin preparations, i.e. at 4% or 5% of proteins than for the most concentrated preparations, i.e. at 20% of proteins.

Apart from the fact that the detection of these insoluble particles requires the rejection of the concerned vials in the final inspection within the framework of quality control, which results in an economic loss, the appearance of these particles during the pasteurization indicates a certain denaturing of the product which may cast a doubt about its good tolerance in the possible administration in man.

An object of the invention is to overcome this drawback by proposing a process for stabilizing human albumin solutions for the purpose of their treatment with heat in a container, in particular the final container, permitting a perfect stabilization and resulting in an albumin solution compatible with the normal use of these solutions.

The invention provides a process for stabilizing human albumin solutions for therapeutic use for the purpose of their treatment with heat in a container, in particular in the final container, comprising adding, in addition to the usual stabilizing formula, a surface active agent selected from Tween 80 (polysorbate 80, the firm Atlas—oleate of polyoxyethylene sorbitan), Tween 20 (the firm Atlas—laurate of polyoxyethylene sorbitan), laurate of polyethylene glycol 600 (the firm Gattefosse), Pluronic F68 (the firm Ugine Kuhlman—copolymer of polyoxyethylene and of polyoxypropylene) or any other equivalent agent.

The surface active agent employed in the process of the invention does not perform the same function as the usual stabilizing formula and therefore cannot be substituted therefor. Indeed, the appearance of particles owing to the pasteurization does not result from the same causes which were the origin of the use of the usual stabilizers, as will be illustrated hereinafter, but from the interactions of the solution with the wall of the container in the course of the thermal treatment.

This phenomenon is observed in conventional vials of neutral glass, for example glass of the borosilicated type I or glass of type II neutralized on the surface by treatment with sulfur dioxide or ammonium sulfate such as described in the European and U.S.A Pharmacopoeias (the firm SAINT-GOBAIN DESJONQUERES), but also in bottles of plastics material, for example of polystyrene (the firm CORNING). This phenomenon probably causes the intervention of denaturing hydrophobic interactions between the product and the wall of the vials.

Usual stabilizing solution is intended to mean in particular sodium caprylate, sodium acetyl tryptophanate, sodium mandelate or a mixture of two or three thereof.

Equivalent agents are intended to mean any agent, in particular any non-ionic surface active agent which prevents, preferably at a low concentration, the denaturing of the albumin by the wall of the container and consequently the formation of insoluble particles when pasteurizing the albumin solutions, and the presence of which in the final solution is not incompatible with the normal use of the solution.

The surface active agents, in particular the non-ionic surface active agents and the like according to the invention must preferably be effective at low concentrations.

According to the invention, the concentrations are advantageously between 5 and 50 mg/l of solution to be stabilized. About 0.25 to 1 molecule of a suitable surface active agent is sufficient for 100 molecules of albumin respectively in a 200 to 50 g/l solution, to prevent the denaturing and the appearance of insoluble particles after pasteurization in the presence of the usual stabilizing formula.

The preferred surface active agent is Tween 80 having a mean molecular weight of 1320 Dalton. It must be used at a concentration higher than 5 mg/l and preferably between 10 and 20 mg/l. A concentration of Tween 80 of 10 mg/l of solution to be stabilized, for a 50 g/l solution of albumin corresponds to 1 molecule of this stabilizer for 100 molecules of albumin.

In a particular embodiment of the invention, the surface active agent is added at an early stage of the manufacture of the albumin. In such a case, the initial concentration of surface active agent must be such that the residual content of the latter at the moment of the pasteurization is sufficient to ensure the desired protecting effect.

The human albumin solutions concerned by the invention are in particular all the protein solutions whose albumin is the majority protein component, i.e. represents more than 80% of all of the proteins and which are intended to be used in human clinical treatment. They are defined, in particular, in the European Pharmacopoeia IInd edition of 1984 under the title "Albumini humani solutio" and in the Code of Federal Regulations of the U.S.A., edition of Apr. 1, 1986 under the title "Albumin (human)" and "Plasma protein fraction (human)".

The human albumin concerned by the invention is in particular obtained by the extraction and purification by any suitable process from a human albumin source or even the culture of animal or plant cells, of bacteria or yeasts transformed for producing human albumin with the aid of genetic engineering techniques. Among the processes suitable for the extraction and purification of human albumin may be mentioned in particular fractionating the plasma with alcohol as described by COHN et al. (4) or fractionating the placental blood with alcohol and zinc as described by TAYLOR et al. (5) or fractionating the placental blood with alcohol, sodium caprylate and alumina gel as described by LIAUIAUD et al. (6) or fractionating the placental blood with alcohol and by chromatography such as described by TAYOT et al. (7) or fractionating plasma by chromatography such as described in the U.S. Pat. No. 4,675,384.

The invention will now be illustrated by non-limitative examples.

EXAMPLE 1

It was attempted to improve the stability of a 50 g/l solution of albumin obtained by dividing placental blood into fractions with alcohol and by chromatography as described by TAYLOR et al. (4). The albumin obtained has a protein purity of 100% by electrophoresis analysis on cellulose acetate and in bidimensional immuno-electrophoresis (presence of a single peak).

The test consisted in increasing the quantities of conventional stabilizers sodium caprylate and sodium acetyl tryptophanate relative to the quantities required by the U.S.A Pharmacopoeia while maintaining a content of sodium of 145 meq/l and a pH of 7.0. The albumin was filtered and then divided up into 100 ml vials of glass of Type I and pasteurized at 60° C. for 10 hours in a water bath. The vials were inspected before and after pasteurization and spontaneous cooling in the air. No vial had any visible particle before the pasteurization.

TABLE I

|  | sodium caprylate mmole/g prot. | sodium acetyl tryptophanate mmole/g prot. | Presence of visible particles after pasteurization |
|---|---|---|---|
| Standard formula U.S.A. Pharmacopoeia | 0.08 | 0.08 | +++ |
| Formula 2 | 0.08 | 0.32 | +++ |
| Formula 3 | 0 | 0.64 | +++ |
| Formula 4 | 0.3 | 0.08 | +++ |
| Formula 5 | 0.64 | 0 | +++ |

It is found (see Table I) that the conventional stabilizers, notwithstanding the highly increased doses, do not permit avoiding the presence of particles in the pasteurized vials. This confirms the fact that the gelling prevented by the conventional stabilizers and the formation of particles are two physically independent phenomena.

EXAMPLE 2

In starting with a placental albumin prepared as in Example 1, 200 g/l, 50 g/l and 10 g/l solutions of proteins were prepared and stabilized with a standard stabilizing formula, namely 0.08 mmole of sodium caprylate/g of protein and 0.08 mmole of sodium acetyl tryptophanate/g of protein. The sodium was adjusted at 145 meq/l with sodium chloride and the pH was adjusted at 7.0. 0 or 5 or 10 mg/l of Tween 80 were then added to the solutions and the solutions filtered and placed in 100 ml vials of glass of Type I, then pasteurized at 60° C. for 10 hours in a water bath. No vial had a visible particle before pasteurization.

TABLE II

|  | Concentration of albumin (g/l) | | | | | | | | |
|---|---|---|---|---|---|---|---|---|---|
|  | 10 | | | 50 | | | 200 | | |
|  | Content of Tween 80 (mg/l) | | | | | | | | |
|  | 0 | 5 | 10 | 0 | 5 | 10 | 0 | 5 | 10 |
| Presence of visible particles after pasteurization | +++ | + | 0 | +++ | + | 0 | ++ | + | 0 |

It is found (see Table II) that the Tween 80 completely prevents the formation of visible particles at the dose of 10 mg/l whatever the concentration of albumin in the solution.

EXAMPLE 3

An attempt was made to improve the stability of a 50 g/l solution of albumin obtained by dividing the plasma into fractions by COHN's method. The albumin was supplied in the lyophilized form by the firm HYLAND. The powder was put in solution and adjusted at 50 g/l of proteins and stabilized with a standard stabilizing formula, namely 0.08 mmole of sodium caprylate/g of protein et 0.08 mmole of sodium acetyl tryptophanate/g of protein. The sodium was adjusted at 145 meq/l with sodium chloride and the pH was adjusted at 7.0. 10 mg/l of Tween 80 were added to a part of this solution The two solutions obtained were filtered and put in100 ml vials of glass of Type I and then pasteurized at 60° C. for 10 hours in a water bath. No vial had visible particles before pasteurization.

TABLE III

|  | Content of Tween 80 (mg/l) | |
| --- | --- | --- |
|  | 0 | 10 |
| Presence of visible particles after pasteurization | +++ | 0 |

It is found (see Table III) that the Tween 80 at the dose of 10 mg/l completely prevents the formation of visible particles in the albumin of COHN at 50 g/l subjected to a pasteurization at 60° C. for 10 hours.

BIBLIOGRAPHY

1. GERETY R. J., ARONSON D. L. Plasma derivatives and viral hepatitis Transfusion 1982: 22(5): 347–51

2. HOROWITZ B et al. Inactivation of viruses in labile blood derivatives II Physical methods. Transfusion 1985: 25(6): 523–527.

3. N. G. P. K., DOBKIN M. B. Pasteurization of antihemophilic factor and model virus inactivation studies Thromb Res 1985: 39(4): 439–447.

4. COHN E. J., et al Préparation and Properties of serum and plasma proteins IV: A system for the separation into fractions of protein and lipoprotein components of biological tissues and fluids J. Am. Chem. Soc. 1946: 68: 459–75.

5. TAYLOR H. L., et al. An improved Procedure for the Preparation of human serum albumin from placental extracts J. Am. Chem Soc. 1956; 78: 1353–55.

6. LIAUTAUD J., et al Préparation de l'albumine humaine á partir de sang hémolysé extrait de placentas congelés. I—Technique de préparation et qualité du produit. Proceeding of the 13 th International Congress of the International Association of Biological Standardization, Budapest 1973—Part A: purification of proteins. Develop. Biol. Standard. 1974; 27: 107-14.

7. TAYOT J. L. et al. Chromatographie industrielle, production et qualité de l'albumine humaine d'origine placentaire. Réunion Coopération internationale et Dérivés Sanguins, Talloires 1981-ED. Fondation Marcel MERIEUX 1982: 47–59.

We claim:

1. Process for stability human albumin solutions for therapeutic use for the purpose of treatment thereof with heat in a container, in particular in a final container, said process comprising adding a usual stabilizing formula to protect albumin against a direct denaturing by heat, adding a surface active agent selected from the group consisting of Tween 80, Tween 20, Pluronic F68 and laurate of polyethylene glycol 600.

2. Process according to claim 1, comprising employing the surface active agent at a concentration ranging from 5 to 50 mg/l.

3. Process according to claim 1, comprising employing the Tween 80 at a concentration higher than 5 mg/l.

4. Process according to claim 3, wherein said concentration is between 10 mg/l and 20 mg/l.

5. Process according to claim 1, comprising adding to the human albumin solution to be stabilized the usual stabilizing formula, adjusting the sodium at 145 meq/l with sodium chloride and the pH at 7.0, adding the surface active agent, filtering, placing the solution in vials, and pasteurizing the solution at 60° C. for 10 hours.

6. Process according to claim 5, wherein said usual stabilizing formula comprises 0.08 mmole of sodium caprylate and 0.08 mmole of sodium acetyl tryptophanate per gram of albumin.

7. Process according to claim 1, comprising adding said surface active agent at an early stage of the manufacture of the albumin.

8. Human albumin solution obtained by a process for stabilizing the human albumin solution for therapeutic use for the purpose of the treatment thereof with heat in a container, in particular in a final container, said process comprising adding an usual stabilizing formula, adding a surface active agent selected from the group consisting of Tween 80, Tween 20, Pluronic F68, laurate of polyethylene glycol 600 and any other equivalent agent.

9. Process according to claim 1 wherein said usual stabilizing formula comprises sodium caprylate and/or sodium acetyltrytophanate and/or sodium mandelate.

* * * * *